United States Patent
Berube

(10) Patent No.: US 6,527,768 B2
(45) Date of Patent: Mar. 4, 2003

(54) END-FIRING MICROWAVE ABLATION INSTRUMENT WITH HORN REFLECTION DEVICE

(75) Inventor: Dany Berube, Fremont, CA (US)

(73) Assignee: AFx Inc., Fremont, CA (US)

( * ) Notice: Subject to any disclaimer, the term of this patent is extended or adjusted under 35 U.S.C. 154(b) by 0 days.

(21) Appl. No.: 09/861,027

(22) Filed: May 18, 2001

(65) Prior Publication Data

US 2001/0029368 A1 Oct. 11, 2001

Related U.S. Application Data

(62) Division of application No. 09/333,747, filed on Jun. 14, 1999, now Pat. No. 6,287,302.

(51) Int. Cl.[7] ............................................... A61F 18/18
(52) U.S. Cl. ........................................ 606/33; 607/98
(58) Field of Search ............................. 606/32–35, 41; 607/96, 98, 99, 101, 154

(56) References Cited

U.S. PATENT DOCUMENTS 4,462,412 A * 7/1984 Turner .................. 607/154
4,641,649 A   2/1987 Walinsky et al.
5,246,438 A   9/1993 Langberg
5,314,466 A   5/1994 Stern et al.
5,405,346 A   4/1995 Grundy et al.
5,800,494 A   9/1998 Campbell et al.

* cited by examiner

*Primary Examiner*—Rosiland S. Kearney
(74) *Attorney, Agent, or Firm*—Ross M. Carothers

(57) ABSTRACT

A microwave ablation instrument including a transmission line having a first conductor and a second conductor suitable for the transmission of microwave energy. A horn antenna device is mounted to the end of the transmission line, and include an outer conductor and an inner conductor. The outer conductor of the horn antenna is electrically coupled to the second conductor of the transmission line, and includes a peripherally extending interior wall flaring outwardly to define a recess therein. The inner conductor of the horn antenna is electrically coupled to the first conductor of the transmission line and terminates in the outer conductor recess. The inner conductor and the outer conductor cooperate to emit an electromagnetic field sufficiently strong to cause tissue ablation in a direction generally away from the flared interior wall of the outer conductor.

18 Claims, 4 Drawing Sheets

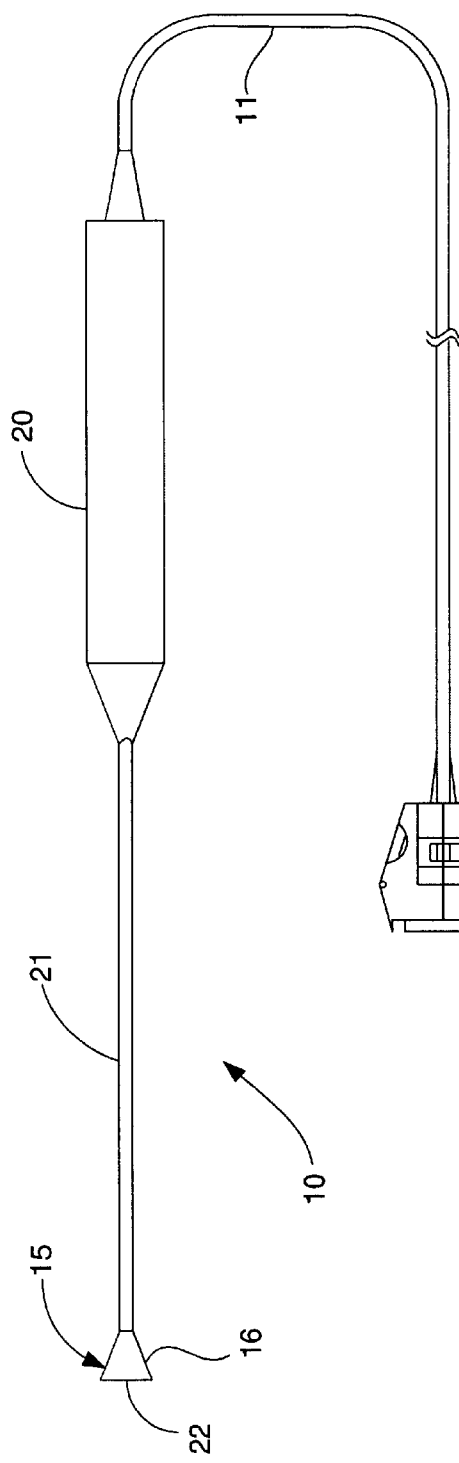
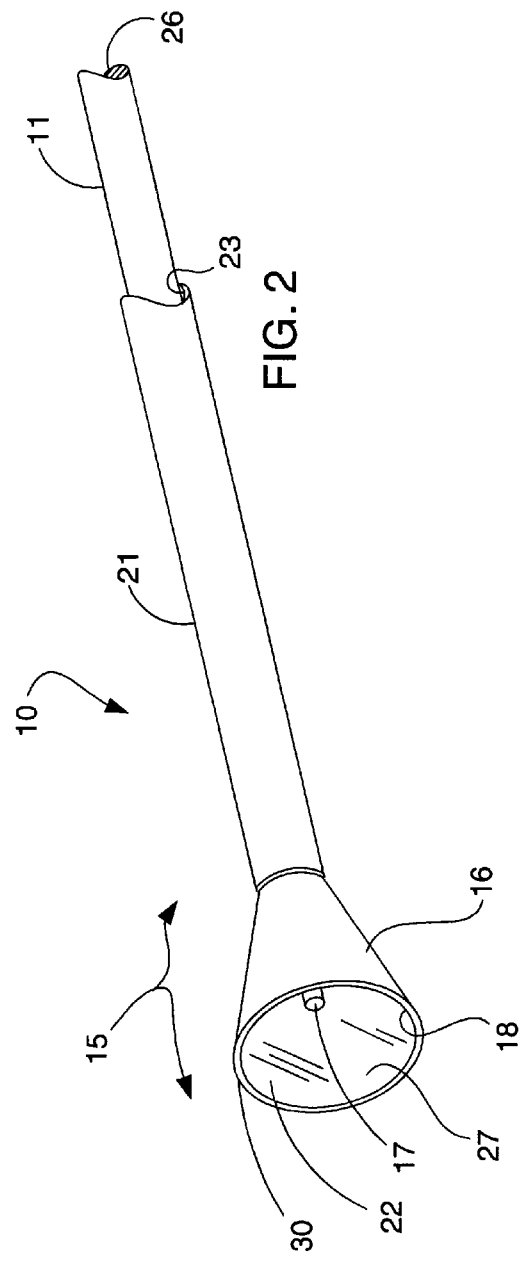
FIG. 1
FIG. 2

END-FIRING MICROWAVE ABLATION INSTRUMENT WITH HORN REFLECTION DEVICE

This application is a Division of Ser. No. 09/333,747 filed Jun. 14, 1999, now U.S. Pat. No. 6,287,302.

BACKGROUND OF THE INVENTION

The present invention relates to ablation instrument systems that use electromagnetic energy in microwave frequencies to ablate internal bodily tissues. More particularly, the present invention relates to an antenna arrangement in an ablation instrument system that directs the microwave energy in a selected direction.

Catheter ablation has recently become an important therapy for certain cardiac arrhythmias, cardiac disrhythmias and tachycardia. Many ablation instrument systems utilize radio frequency (RF) energy as the ablating energy source. accordingly, a variety of RF based catheters and power supplies are currently available to electrophysiologists. However, radio frequency energy has several limitations including the rapid dissipation of energy in surface tissues resulting in shallow "burns" and failure to access deeper arrhythmic tissues. Another limitation of RF ablation instruments is the risk of clot formation on the energy emitting electrodes. Such clots have an associated danger of causing potentially lethal strokes in the event that a clot is dislodged from the ablation instrument.

A second common ablation approach is the use of high voltage, direct current defibrillator discharges. Direct current ablation has several drawbacks including the need for general anesthesia and explosive discharges that can cause debris or even rupture certain cardiac organs. For these and other reasons, significant attention has been given recently to alternative ablative energy sources.

Microwave frequency energy has long been recognized as an effective energy source for heating biological tissues and has seen use in such hyperthermia applications as cancer treatment and preheating of blood prior to infusions. In view of the drawbacks of the traditional catheter ablation techniques, there has recently been a great deal of interest in using microwave energy as an ablation energy source. The advantage of microwave energy is that it is much easier to control and safer to apply than direct current applications. Moreover, microwave energy is capable of generating substantially larger lesions than RF catheters, which greatly simplifies the actual ablation procedures. Accordingly, there are a number of catheters under development which utilize electro-magnetic energy in the microwave frequency range as the ablation energy source. By way of example, such systems are described in the U.S. Pat. No. 4,641,649 to Walinsky; U.S. Pat. No. 5,246,438 to Langberg: U.S. Pat. No. 5,405,346 to Grundy, et al.; and U.S. Pat. No. 5,314,466 to Stern, et al, each of which is incorporated herein by reference.

While these microwave ablation instruments may be employed to adequately ablate bio-tissue, most of the existing microwave ablation instruments contemplate the use of longitudinally extending helical antenna coils that direct the electromagnetic energy in a direction that is generally perpendicular to the longitudinal axis of the instrument although the fields created are not well constrained to the antenna itself. Although such instrument designs work well for a number of applications, it would also be desirable to provide microwave ablation instrument designs that are capable of effectively transmitting electromagnetic energy in other specific directions, such as a generally forward direction relative to the longitudinal axis of the instrument.

One such end-firing ablation instrument is disclosed in our U.S. Pat. No. 5,800,494. This instrument design incorporates a coaxial transmission line having an inner conductor, an outer conductor and a dielectric material medium disposed therebetween. At the distal end of the inner conductor is a spirally wound antenna coil adapted and oriented to emit an electromagnetic field in a direction distal to the longitudinal axis at the tip of the inner conductor.

Although this design provides functional distal firing capabilities, the width of the electromagnetic field is only about 2–4 mm wide. Accordingly, without substantially increasing the antenna dimensions and/or power output, use of the ablation instrument is limited to relatively small target regions.

SUMMARY OF THE INVENTION

The present invention provides a microwave ablation instrument including a transmission line having a first conductor and a second conductor suitable for the transmission of microwave energy, and having a proximal end thereof coupled to a microwave energy source. The ablation instrument further includes a horn antenna device having an outer conductor and an inner conductor. The outer conductor of the horn antenna is electrically coupled to the second conductor of the transmission line, and includes a peripherally extending interior wall flaring outwardly to define a recess therein. The inner conductor of the horn antenna is electrically coupled to the first conductor of the transmission line and terminates in the outer conductor recess. The inner conductor and the outer conductor cooperate to emit an electromagnetic field sufficiently strong to cause tissue ablation in a direction generally away from the flared interior wall of the outer conductor.

In one embodiment, the outer conductor of the antenna device is integrally formed with the outer second conductor of the transmission line. The inner conductor of the antenna device is further integrally formed the inner first conductor of the transmission line.

In another aspect, the line dielectric material includes a first dielectric constant, and the antenna dielectric material includes a second dielectric constant. A proximal face of the antenna dielectric material is in conductive contact with the line dielectric material, and a distal face of the antenna dielectric material is spaced-apart from the proximal face by a predetermined distance enabling resonance of the emitted electromagnetic field at the distal face proportionately based upon the first dielectric constant and second dielectric constant.

In another embodiment of the present invention, a horn antenna assembly is provided for use with a microwave ablation instrument including a coaxial transmission line having a line inner conductor and a line outer conductor separated by a line dielectric material. The horn antenna assembly includes an antenna outer conductor electrically coupled to the line outer conductor. The antenna outer conductor includes a peripherally extending interior wall defining a recess and which flares outwardly from a proximal end to a distal end thereof. An antenna inner conductor is electrically coupled to the line inner conductor and adapted to terminate in the recess of the antenna outer conductor. The antenna inner conductor and the antenna outer conductor cooperate to emit an electromagnetic field sufficiently strong to cause tissue ablation. This field is radiated in a direction generally away from the distal end of the horn antenna assembly. The present inventive horn assembly further includes an antenna dielectric material having a second dielectric constant and being disposed in the recess of the antenna outer conductor. The antenna dielectric material includes a proximal face in conductive contact with the line dielectric material and a distal face spaced-apart from the proximal face by a predetermined distance enabling resonance of the emitted electromagnetic field at the distal face. This resonance is proportionately based upon a first dielectric constant of the line dielectric material and the second dielectric constant of the antenna dielectric material.

In one configuration, an impedance matching device is included having a third dielectric constant. A proximal face of the impedance matching device is in conductive contact with the distal face of the antenna dielectric material, and a distal face of the impedance matching device is formed for direct contact with a targeted tissue to be ablated. The distal face of the impedance matching device is spaced-apart from the proximal face thereof by a second predetermined distance. The third dielectric constant and the second predetermined distance cooperate with electromagnetic field discharged from the antenna dielectric material distal face such that the impedance of the emitted electromagnetic field at the distal end of the impedance matching device is substantially matched with the impedance of the tissue to be ablated.

In still another embodiment, a microwave ablation instrument includes a coaxial transmission line including a line inner conductor and a line outer conductor separated by a line dielectric material. The transmission line, having a first dielectric constant, defines a transmission face thereof, and a proximal end thereof coupled to a microwave energy source. An antenna device is coupled to the transmission line at the transmission face to emit an electromagnetic field sufficiently strong to cause tissue ablation. The antenna device further includes an antenna dielectric material having a proximal face in conductive contact with the line transmission face, and a distal face spaced-apart from the line proximal face. An interference device is positioned in the first dielectric material between the line outer conductor and the line inner conductor, and further at a location behind the line transmission face. The interference device is spaced-apart from the distal face of the dielectric material a predetermined distance such that resonance is created in the horn antenna.

In another embodiment, the interference device is provided by an annular ridge having a reflection face extending from the line outer conductor towards the line inner conductor. The reflection face is preferably substantially planar and substantially parallel to the distal face of the antenna dielectric material. In another arrangement, the annular ridge includes a transition wall portion extending rearwardly from the reflection face, and smoothly tapering from the reflection face to the outer conductor.

BRIEF DESCRIPTION OF THE DRAWINGS

The assembly of the present invention has other objects and features of advantage which will be more readily apparent from the following description of the Detailed Description of Preferred Embodiments and the appended claims, when taken in conjunction with the accompanying drawing, in which:

FIG. 1 is top plan view of a microwave ablation instrument system having a horn antenna device constructed in accordance with the present invention.

FIG. 2 is an enlarged, fragmentary, top perspective view the horn antenna device of FIG. 1.

DETAILED DESCRIPTION OF PREFERRED EMBODIMENTS

Figure 3:
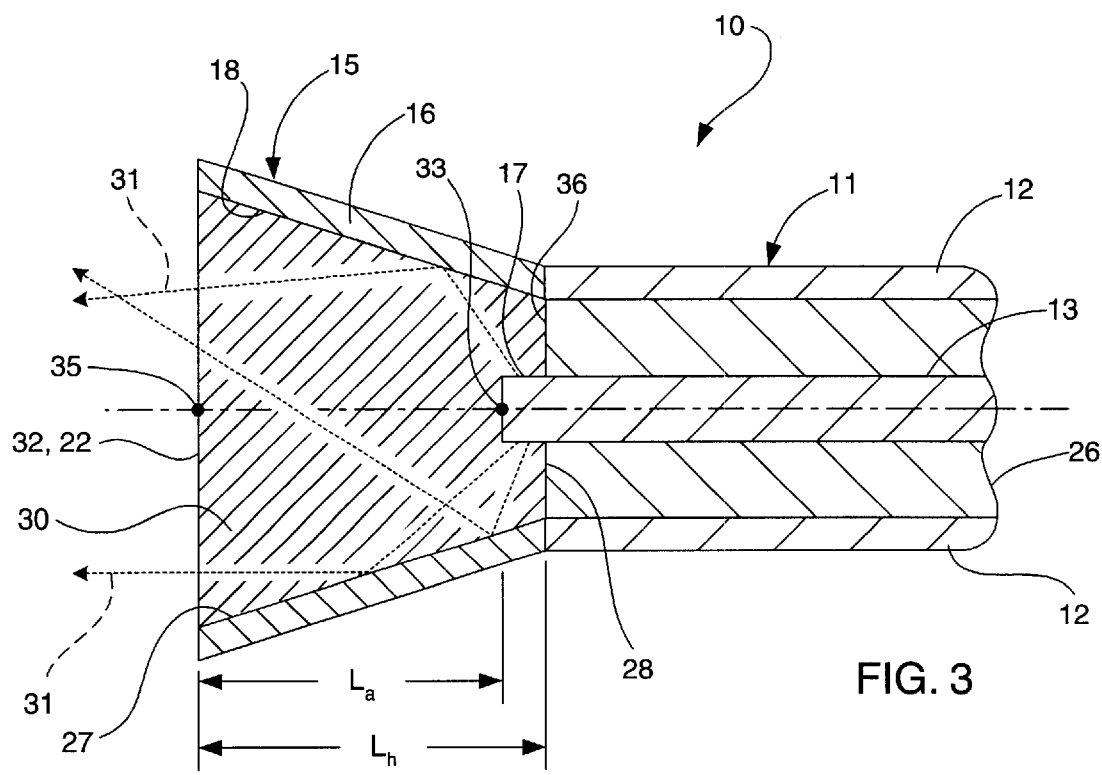
FIG. 3 is an enlarged, fragmentary side elevation view, in cross-section of the horn antenna device of FIG. 2.

While the present invention will be described with reference to a few specific embodiments, the description is illustrative of the invention and is not to be construed as limiting the invention. Various modifications to the present invention can be made to the preferred embodiments by those skilled in the art without departing from the true spirit and scope of the invention as defined by the appended claims. It will be noted here that for a better understanding, like components are designated by like reference numerals throughout the various figures.

Referring now to FIGS. 1–3, a microwave ablation instrument, generally designated 10, is provided including a transmission line 11 having a first conductor 12 and a second conductor 13 (FIG. 3) suitable for the transmission of microwave energy, and having a proximal end connector 25 thereof coupled to a microwave energy source (not shown). The ablation instrument 10 further includes a horn antenna device, generally designated 15, having an antenna outer conductor 16 and an antenna inner conductor 17. The outer conductor 16 of the horn antenna device 15 is electrically coupled to the second conductor 13 of the transmission line 11, and includes a peripherally extending interior wall 18 flaring outwardly to define a recess therein. The inner conductor of the horn antenna is electrically coupled to the first conductor of the transmission line and terminates in the outer conductor recess. The inner conductor and the outer conductor cooperate to emit an electromagnetic field sufficiently strong to cause tissue ablation in a direction generally away from the flared interior wall of the outer conductor.

Accordingly, a microwave ablation instrument is provided that utilizes a horn antenna design to create an end-fire electromagnetic field for ablating biological tissue. Advantageously, this horn antenna arrangement reflects and focuses the microwave energy emitted radially from the antenna inner conductor generally in a direction away from the horn assembly (FIG. 3). A more concentrated electromagnetic energy field can thus be directed toward a region distal to the horn antenna thereby allowing for deeper penetration of biological tissues. Moreover, the effective ablation area is substantially increased over current end-firing ablation instruments which typically utilize transverse mounted helical coils as the antenna structure, while maintaining ablation accuracy of the targeted tissue. The targeted tissues, as a consequence, can be ablated without impacting the surrounding untargeted tissues.

It will be appreciated that the term "end-fire" herein encompasses electromagnetic fields that have a significant component directed to a controlled region distal to the horn antenna assembly. Tissue ablation can thus be more strategically controlled, directed and performed without concern for undesirable ablation of other adjacent tissues which may otherwise be within the electromagnetic ablation range radially emanating from the antenna. This "end-fire" ablation instrument is thus particularly suitable for ablation procedures requiring accurate tissue ablations or lesion formation such as those reserved for open-chest or minimally invasive MAZE III procedures to treat atrial arrhythmias, or for cardiac disrhythmias and tachycardia.

In the preferred embodiment, the ablation instrument 10 includes a handle 20 coupled to the horn antenna device 15 through an elongated tubular shaft 21. By manually manipulating the handle 20, the distal contact surface 22 of the horn antenna assembly may be oriented and positioned against the targeted tissue to perform the desired ablation.

The shaft 21 is preferably provided by a metallic hypotube which the horn assembly may be supported through brazing paste, welding or the like. Moreover, the shaft 21 is preferably bendable and malleable in nature to enable shape reconfiguration to position the antenna and the cradle device at a desired orientation relative the handle. This enables the surgeon to appropriately angle the distal contact surface 22 toward the targeted region for tissue ablation. It will be appreciated, however, that the material of the shaft is further sufficiently rigid, although bendable, so that the shaft is not easily deformed upon the application of pressure during ablative use. Such materials, for example, includes stainless steel or aluminum having diameters ranging from about 0.090 inches to about 0.200 inches with wall thickness ranging from about 0.050 inches to about 0.025 inches. Most preferably, the shaft is 304 stainless steel having an outer diameter of about 0.120 inches and a wall thickness of about 0.013 inches.

While the embodiment is described and illustrated in combination with the tubular shaft 21, it will be appreciated that a sufficiently rigid, yet bendable, transmission line 11 may displace the shaft in most instances.

The transmission line 11, as shown in FIGS. 1 and 2, extends through handle 20 and into a passage 23 of the tubular shaft 21 for electrical coupling to the distally mounted horn antenna assembly. At a proximal end of the transmission line 11 is an electrical connector 25 which electrically couples the horn antenna device 15 to an external power supply (not shown). Typically, the transmission line 11 may be provided by any type transmission line that is capable of transmitting microwave energy (e.g., coaxial cable, rectangular wave guides, stripline, slotline, microstripline). In the preferred form, however, the transmission line is provided by a semi-rigid coaxial transmission line having a line inner conductor 12, a line outer conductor 13 and a line dielectric material 26 disposed between line inner conductor 12 and outer conductor 13. The line inner and outer conductors in any of the above embodiments may be composed of any suitable conductive material that can transmit microwave energy such as copper, silver or gold wire, plated wires such as silver plated copper, aluminum, and the like. In addition, the transmission line 11 may include a flexible outer tubing (not shown) to add rigidity and to provide protection to the outer conductor.

Briefly, the power supply (not shown) includes a microwave generator which may take any conventional form. When using microwave energy for tissue ablation, the optimal frequencies are generally in the neighborhood of the optimal frequency for heating water. By way of example, frequencies in the range of approximately 800 MHz to 6 GHz work well. Currently, the frequencies that are approved by the U.S. Food and Drug Administration for experimental clinical work are 915 MHz and 2.45 GHz. Therefore, a power supply having the capacity to emit microwave energy at frequencies in the neighborhood of 2.45 GHz may be chosen. At the time of this writing, solid state microwave generators in the 1–3 GHz range are expensive. Therefore, a conventional magnetron of the type commonly used in microwave ovens is utilized as the generator. It should be appreciated, however, that any other suitable microwave power source could be substituted in its place, and that the explained concepts may be applied at other frequencies like about 434 MHz, 915 MHz or 5.8 GHz (ISM band).

A frequent concern in the management of microwave energy is impedance matching of the various transmission line components with that of the power source. An impedance mismatch will reflect some portion of the incident power back to the power source resulting in reduced energy transmission and increased losses, typically manifested as heat generation due to line or wave guide attenuation. Reflected power can heat the transmission cable and generator causing substantial damage. More importantly, a heated transmission line may potentially burn a patient during the ablation process. Accordingly, it is desirable to match the impedance of the transmission line with the incident power of the power source, which is typically on the order of fifty (50) ohms. If the impedance is properly matched, substantially all the power may be transmitted through the line and reflections may be minimized. The transmission line 11 is therefore provided by a conventional fifty (50) ohm coaxial design suitable for the transmission of microwave energy at frequencies in the range of about 400 to about 6000 megahertz.

To achieve the above-indicated impedance properties from a relatively small diameter transmission line, the size and materials of the line inner conductor 12, as well as the size, shape and material of the line dielectric material medium 26 must be carefully selected. Each of these variables of the transmission line, together with other factors related to the antenna device, may be used to adjust the impedance and energy transmission characteristics of the antenna device.

In accordance with one aspect of the present invention, the horn antenna devices 15 is formed by flaring outwardly the distal portion of the line outer conductor 13 to form the antenna outer conductor 16. The antenna outer conductor 16 is therefore integrally formed with line outer conductor 13. Accordingly, the inner peripheral wall 18 of the horn antenna preferably defines a conical shaped recess 27 upon which the antenna inner conductor terminates.

As shown in FIG. 3, the distal portion of line inner conductor 12 terminates in the recess 27 of the horn antenna device 15 to form the antenna inner conductor 17. Thus, the antenna inner conductor 17 is also essentially integrally formed with the line inner conductor 12.

It will be appreciated, however, that both the antenna outer and inner conductors may be provided by any conductive independent structure, such as spring steel, aluminum, beryllium copper, or silver-plated copper, which is conductively coupled to the respective line outer and inner conductor without departing from the true spirit and nature of the present invention. The conductive mounting of either antenna conductor may be performed through soldering, brazing, ultrasonic welding or adhesive bonding or the like.

The distal section of the line inner conductor 12 preferably extends past the proximal face 28 of the antenna dielectric material 30 to form a monopole antenna (i.e., the antenna inner conductor 17). The radiation pattern of the antenna inner conductor, therefore, is radially emitted in a substantially cylindrical manner, and is consistent with the length thereof. However, since the inner peripheral wall 18 of the antenna outer conductor 16 is flared outwardly, the electromagnetic radiation emitted by the antenna inner conductor 17 will be reflected and redirected off the inner peripheral wall in directions distal to the horn antenna assembly (represented by arrows 31 in FIG. 3).

This distally redirected and reflected microwave energy is distributed with greater accuracy, and with less dispersion than a conventional monopole antenna without a horn reflector. The microwave energy directed toward the targeted tissue can therefore be intensified without having to increase the antenna output. As a consequence, this more concentrated microwave energy enables deeper biological tissue penetration. Moreover, as compared to current end-firing microwave ablation designs, such as the above discussed U.S. Pat. No. 5,800,494, the usable ablation area is substantially increased.

To facilitate discussion of this aspect of the present invention, FIG. 3 illustrates a cross-sectional side elevation view of the horn antenna device 15. AS above-mentioned, the antenna outer conductor 16 includes peripherally extending interior wall 18 flaring outwardly from the proximal face 28 of the dielectric material 30 to the distal face 32 thereof. This outward flare of the interior wall 18 is generally linear in profile, and collectively forms a conical-shaped outer conductor. The outward flare, however, may be arcuate, convex, concave, etc. (as long as the flare is outward in totality) to form any conical shaped (e.g., oblique, frustum) or pyramidal shaped (e.g., oblique rectangular, tetrahedral) recess which functions to reflect and redirect the electromagnetic energy distal to the horn antenna device 15.

In the preferred form, the interior wall 18 of the antenna outer conductor 16 is oriented at an acute angle relative the longitudinal axis to redirect the electromagnetic waves distal to the horn assembly. This acute angle is preferably in the range of about 15° to about 75°. Essentially, the smaller the acute angle, the smaller the impact area. However, the reflected and redirected electromagnetic radiation for this smaller impact area is generally more intense. In contrast, the greater the acute angle, the larger the impact area, but the less intense the emitted electromagnetic radiation.

As a general rule, the diameter of the face 38 must be equal to λ/2 where λ is the wavelength in the recess 27 (the wavelength depends on the dielectric constant of the material that filled 27 (dielectric material 30).

Referring back to FIGS. 1 and 3, the antenna dielectric material 30 is shown disposed in the recess 27 of the antenna outer conductor 16. Once the waves propagate through the coaxial transmission line, the electromagnetic wave encounters the antenna dielectric material 30, via the proximal face, before entering the recess 27 of the horn antenna. Subsequently, the electromagnetic waves are emitted from the antenna inner conductor 17 and propagate through the antenna dielectric material 30. The antenna dielectric material 30 must therefore be suitable to facilitate transmission of the electromagnetic waves reflected off the antenna outer conductor, from the proximal face 28 to the distal face 32 thereof, while minimizing absorption of the microwaves. Accordingly, the dielectric material must exhibit the suitable microwave characteristics, for proper operation. In the preferred embodiment, the antenna dielectric material 30 is composed of a silicon and TEFLON® composite, although other suitable materials may be used as well such as ceramic powder, polyethylene and polyolifin.

The distal face 32 of the antenna dielectric material 30 essentially forms a radiative window for the horn antenna device 15 upon which the electromagnetic radiation can be transmitted therefrom. In the preferred embodiment, it is this distal face 32 which generally contacts the targeted biological tissue (i.e., a distal contact surface 22) during ablation, and is therefore preferably substantially smooth and substantially planar. It should be noted, however, that the distal contact surface 22 of the horn antenna may be curvilinear or adapted to the shape of the tissue being ablated to assure conductive contact. Moreover, depending upon the shape of the distal edge of the antenna outer periphery, the distal face will be circular-shaped (i.e., circle, oval, etc.). However, a polygonal-shaped (i.e., square, rectangle, hexagon, etc.) or any other conceivable shape may also be used for the distal face.

To optimize the transfer of the electromagnetic power through the distal contact surface 22 of the antenna dielectric material 30, it is desirable to achieved frequency response in the system or to decrease the reflected power with a "matching network". Transmitted power at the distal contact surface 22 of the antenna dielectric material 30 is thus maximized. Resonance is achieved by positioning the distal end of the antenna inner conductor 17 at a first node 33 of the transmitted wave, while positioning the distal face 32 of the antenna dielectric material 30 at a second node 35 of the transmitted wave (FIG. 3). If will be appreciated that the first node 33 and the second node need not be adjacent nodes in the transmitted wave.

As above indicated, an impedance match between the dielectric components and that of the targeted tissue is an important consideration when selecting the antenna dielectric material composition. Generally, the dielectric properties of the line dielectric material 26 and that of the tissue being ablated are already predetermined. For example, the line dielectric material is chosen to match the impedance with the power source (i.e., at fifty (50) ohms), while the dielectric properties of the targeted bio-tissues are substantially the same for all patients. In the best case scenario, a suitable antenna dielectric material would be chosen having a dielectric constant ($\epsilon_a$) determined by the following equation:

$$\epsilon_a = (\epsilon_l \epsilon_t)^{1/2}$$

where $\epsilon_l$ is the dielectric constant of the line dielectric material 26, and $\epsilon_t$ is the dielectric constant of tissue to be ablated.

Figure 4:
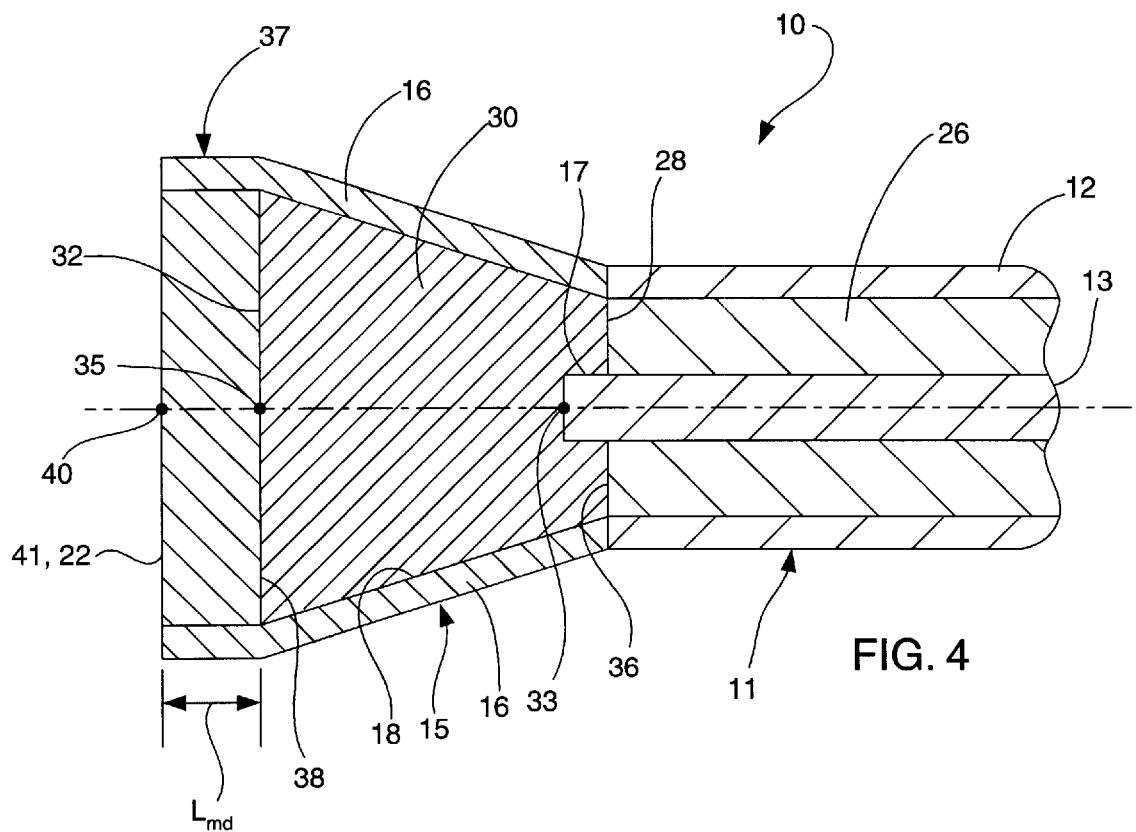
FIG. 4 is a fragmentary side elevation view, in cross-section, of an alternative embodiment of the horn antenna device of FIG. 2 including an impedance matching device.

Referring now to FIG. 4 and in accordance with another aspect of the present invention, a quarter wave transformer device, generally designated 37, may be provided to further facilitate impedance matching, or the power transfer between the horn antenna device 15 and the targeted tissue. Thus, reflection of the electromagnetic wave is further minimized at the tissue surface by physically positioning this device 37 between the antenna dielectric material 30 and the targeted tissue (not shown). Accordingly, the quarter wave transformer 37 includes a proximal face 38 which is placed in conductive contact with a distal face 32 of the antenna dielectric material 30. This device forms a waveguide having and impedance $Z_{md}$ that may be calculated using the following equation:

$$Z_{md} = (\epsilon_t^{1/2} \cdot Z_a)^{1/2}$$

where $\epsilon_t$ is the dielectric constant of the tissue to be ablated and $Z_a$ is the impedance of the horn antenna on the surface port defined by surface 32.

According to multiple dielectric interfaces theory, the physical length of the impedance transformer (37), when $Z_a \sqrt{\epsilon_1}$ (when the impedance of the horn antenna is different from the intrinsic impedance of the tissue to ablate) is given by:

$$L_{md} = \frac{n \cdot \lambda_{md}}{4}$$

where:

n=1, 3, 5, 7, ... and $\lambda_{md}$ is the wavelength in the impedance transformer (37). This wavelength is a function of the propagation mode as well as the geometry of the impedance transformer. In contrast, when $Z_a = \sqrt{\epsilon_1}$, the length $L_{md}$ is calculated by:

$$L_{md} = \frac{n \cdot \lambda_{md}}{2}$$

where: n=1, 2, 3, ....

The dielectric material composition of the impedance matching device 37 must also exhibit suitable microwave properties to facilitate transmission of the electromagnetic waves propagating therethrough, while minimizing absorption of the microwaves. The impedance matching device dielectric material is preferably composed of a silicon and TEFLON® composite having the proper dielectric constant $\epsilon_{md}$. Other proper materials, of course, may be employed such as ceramic powders.

In this arrangement, the distal contact surface 22 corresponds to the distal face 41 of the matching device 37, and functions as the radiative window of the horn antenna device 15. As indicated, this contacting surface is employed to conductively contact the targeted biological tissue during ablation. It should be noted that his distal contact surface 22 may also be curvilinear or adapted to the shape of the tissue being ablated to assure conductive contact.

Figure 5:
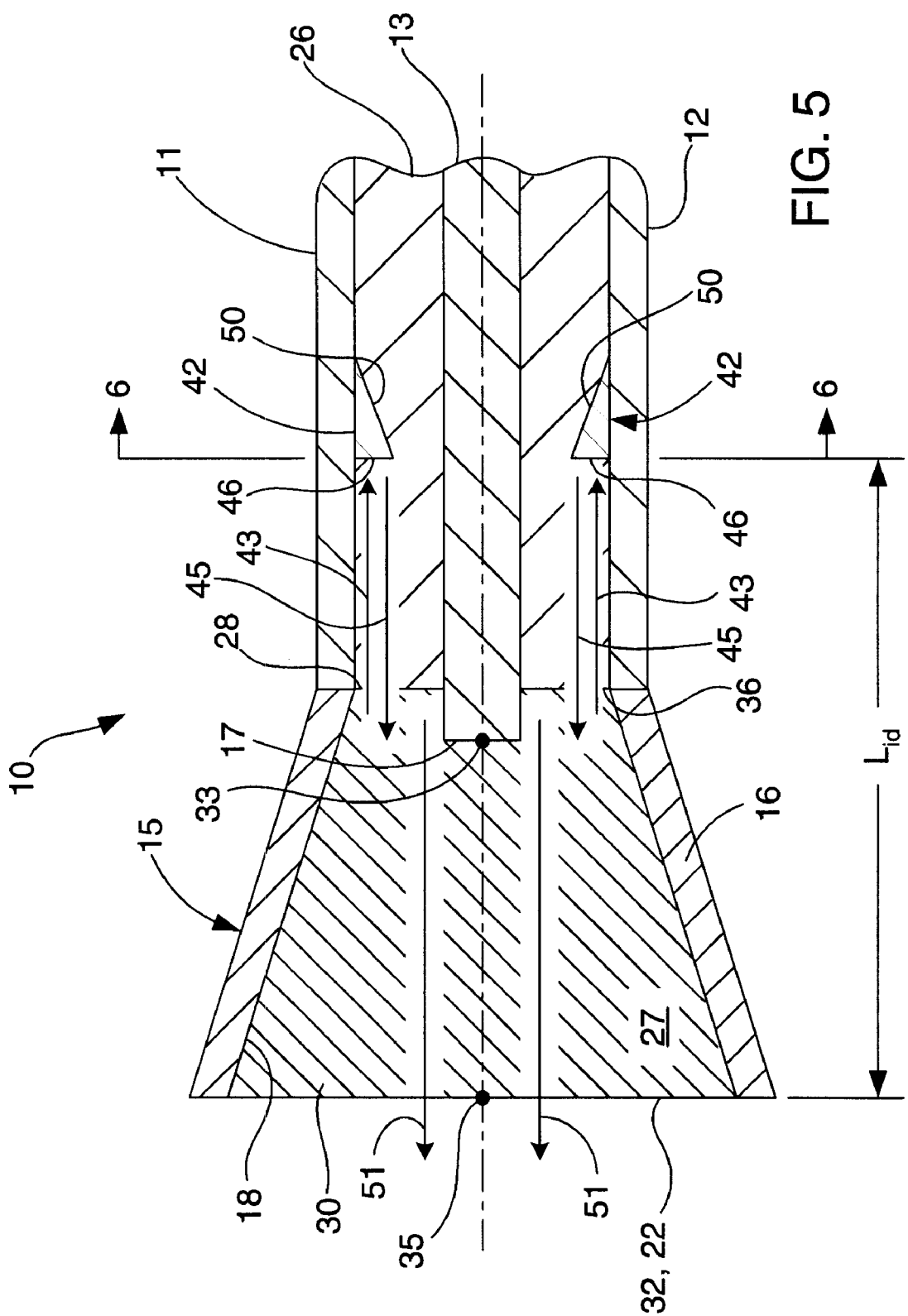
FIG. 5 is an enlarged, fragmentary, side elevation view, in cross-section, of an alternative embodiment of the horn antenna assembly of FIG. 2 having an interference device.
Figure 7:
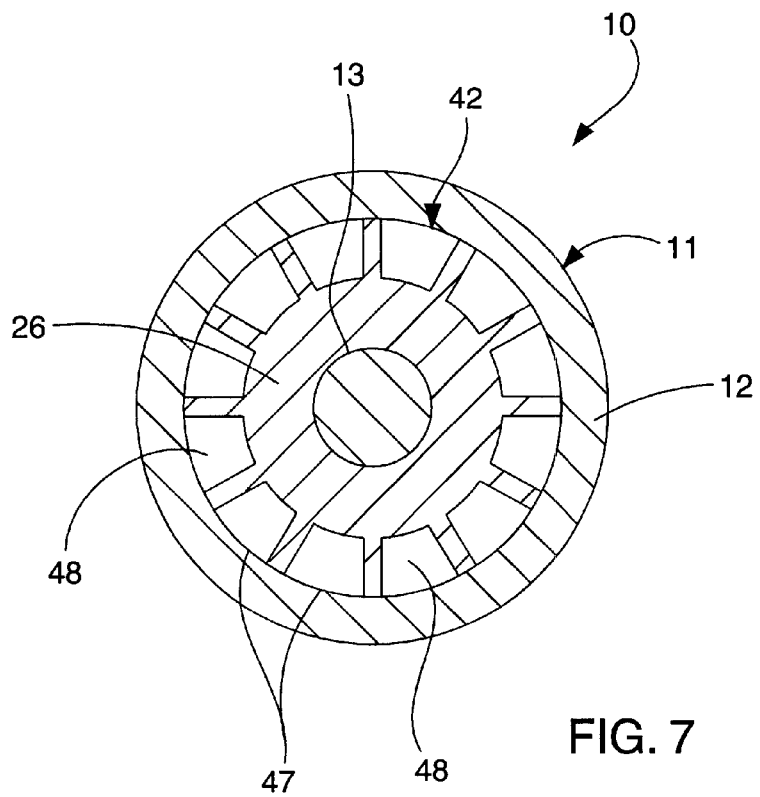
FIG. 7 is an front elevation view, in cross-section, of an alternative embodiment of the interference device of FIG. 6.

Referring now to FIG. 5, another embodiment of the present invention is illustrated which includes an interference device 42 oriented along the path of the propagating incident wave and positioned proximal to the distal contact surface 22 of the horn antenna device 15. In situations where the impedance at the interface between the distal contact surface 22 of the horn antenna device 15 and that of the targeted tissue cannot be or is not sufficiently matched, the reflected electromagnetic wave (represented by arrow 43 in FIG. 5) therefrom can be re-reflected back toward the distal contact surface 22 by the interference device 42 (represented by arrow 45). Accordingly, the reflection of the incident electromagnetic wave caused by the impedance mismatch at the contacting face/tissue interface will travel back toward the power supply until the reflected wave encounters a reflection face 46 of the interference device 42. Consequently, this structural barrier causes a re-reflection (represented by arrow 45) of the reflected wave 43 back toward the distal contact surface 22 of the horn assembly.

To cause a reflection of the reflected electromagnetic wave 43, the interference device 42 is composed of a metallic or dielectric material which creates an impedance mismatch with the dielectric material which the interference device is embedded in. Accordingly, when the reflected wave 43 encounters the sharp transition at the reflection face 46, the reflected wave 43 is re-reflected back toward the distal contact surface of the horn antenna device 15 (represented by arrow 45).

Figure 6:
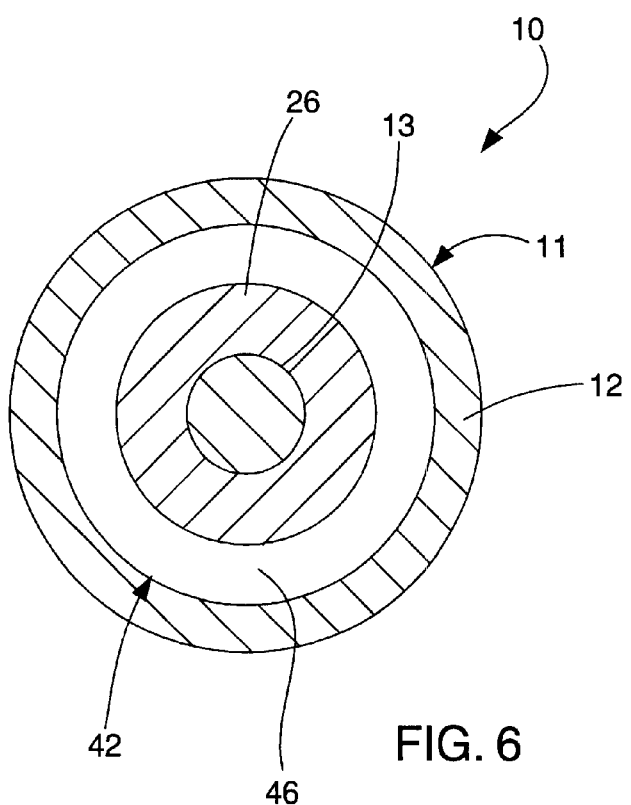
FIG. 6 is an enlarged front elevation view, in cross-section, of the interference device taken substantially along the plane of the line 6—6 in FIG. 5.

Preferably, the interference device 42 is in the shape of an annular ridge which is embedded in the line dielectric material 26 between line outer conductor 12 and line inner conductor 13. FIG. 6 best illustrates that the reflection face 46 of the interference device 42 is preferably ring-shaped, and is oriented substantially perpendicular to the longitudinal axis of the transmission line 11 and substantially parallel to the distal contact surface 22. The radial height of the annular ring is preferably about one quarter (¼) to about three-quarters (¾) the radius of line dielectric material 26, and extends substantially continuously from the line outer conductor 13 towards the line inner conductor 12. The reflection face 46, accordingly, forms a sharp transition barrier which offer a smooth transition for the propagating electromagnetic wave.

In accordance with the present invention, the reflection face 46 of the interference device 42 is spaced-apart from the distal contact surface 22 of horn antenna device 15 by a predetermined distance which causes a constructive interference with the incident electromagnetic wave (represent by arrow 51 in FIG. 5) propagating past the interference device 42 and through the horn antenna assembly. In this manner, a resonance in the horn is created where the phase difference between the incident electromagnetic wave 51 and the re-reflected incident wave (represented by arrow 45) is substantially 0°. Accordingly, the in-phase electromagnetic waves are converged to increase the amplitude and intensity of the electromagnetic field propagating from the interference device through the horn antenna device 15.

Although only a few embodiments of the present inventions have been described in detail, it should be understood that the present inventions may be embodied in many other specific forms without departing from the spirit or scope of the inventions. For example, the interface device may be employed with any of the embodiments described herein. Moreover, the invention has been described in terms of a microwave ablation instrument for cardiac applications, however, it should be appreciated that the described microwave ablation instrument could be used for a wide variety of non-cardiac ablation applications as well. The size and materials of the described antenna may be widely varied.

What is claimed is:

1. A horn antenna assembly for use with a microwave ablation instrument including a coaxial transmission line having a line inner conductor and a line outer conductor separated by a line dielectric material having a first dielectric constant, said horn antenna assembly comprising:

an antenna outer conductor electrically coupled to said line outer conductor and having a peripherally extending interior wall defining a recess, and flaring outwardly from a proximal end to a distal end of the horn antenna assembly;

an antenna inner conductor electrically coupled to said line inner conductor and terminating in said recess of said antenna outer conductor, said antenna inner conductor and said antenna outer conductor cooperating to emit an electromagnetic field sufficiently strong to cause tissue ablation, and in a direction generally away from the distal end of said horn antenna assembly; and an antenna dielectric material having a second dielectric constant and disposed in said recess of said antenna outer conductor, said antenna dielectric material having a proximal face in conductive contact with said line dielectric material and a distal face spaced-apart from said proximal face by a predetermined distance enabling resonance of the emitted electromagnetic field at said distal face proportionately based upon the first dielectric constant and second dielectric constant.

2. The horn antenna assembly of claim 1, wherein said coaxial transmission line is suitable for transmission of microwave energy at frequencies in the range of approximately 400 to 6000 megahertz.

3. The horn antenna of claim 1, wherein the antenna outer conductor is integrally formed with said line outer conductor, and the antenna inner conductor is integrally formed with said line inner conductor.

4. The horn antenna assembly of claim 1, wherein said distal face of said antenna dielectric material is circular-shaped.

5. The horn antenna assembly of claim 1, wherein a distal perimeter of the outer conductor, defining said distal face of said antenna dielectric material, is oval-shaped.

6. The horn antenna assembly of claim 1, wherein said antenna outer conductor is conical-shaped, and said interior wall flares outwardly from the longitudinal axis at an acute angle in the range of about 15° to about 75°.

7. The horn antenna assembly of claim 1 further including:
an impedance matching device having a third dielectric constant, a proximal face in conductive contact with the distal face of the antenna dielectric material and a distal face formed for direct contact with a targeted tissue to be ablated, said distal face of said impedance matching device being spaced-apart from the proximal face thereof by a second predetermined distance, said third dielectric constant and the second predetermined distance cooperating with electromagnetic field discharged from the antenna dielectric material distal face such that the impedance of the emitted electromagnetic field at the distal end of the impedance matching device is substantially matched with the impedance of the tissue to be ablated.

8. The horn antenna of claim 7, wherein the distal face of said impedance matching device is substantially parallel to the distal face of said antenna dielectric material.

9. A microwave ablation instrument comprising:
a coaxial transmission line including a line inner conductor and a line outer conductor separated by a line dielectric material having a first dielectric constant and a transmission face thereof, and having a proximal end thereof coupled to a microwave energy source;
an antenna device coupled to the transmission line at the transmission face for generating an electromagnetic field sufficiently strong to cause tissue ablation, said antenna device further including an antenna dielectric material having a proximal face in conductive contact with the line transmission face and a distal face spaced-apart from the line proximal face; and
an interference device positioned in the first dielectric material between the line outer conductor and the line inner conductor, and at a location behind the line transmission face, said interference device being spaced-apart a predetermined distance from said distal face of the dielectric material such that a resonance is created in the horn antenna.

10. The microwave ablation instrument of claim 9, wherein the interference device is provided by an annular ridge having a reflection face extending from said line outer conductor towards said line inner conductor.

11. The microwave ablation instrument of claim 10, wherein said reflection face is substantially planar and substantially parallel to the distal face of the antenna dielectric material.

12. The microwave ablation instrument of claim 10, wherein said reflection face is of a height between the range of about 0.25 times and about 0.75 times the radius of the line dielectric material.

13. The microwave ablation instrument of claim 10, wherein said reflection face of said annular ridge extends continuously about the line inner conductor.

14. The microwave ablation instrument of claim 10, wherein said interference device is metallic.

15. The microwave ablation instrument of claim 9, wherein said annular ridge includes a transition wall portion extending rearwardly from said reflection face, and smoothly tapering from said reflection face to said outer conductor.

16. The microwave ablation instrument of claim 9, wherein said antenna device includes
an antenna outer conductor electrically coupled to the line outer conductor and having a peripherally extending interior wall flaring outwardly and defining a recess formed for receipt of the antenna dielectric material therein, and
an antenna inner conductor electrically coupled to the line inner conductor and terminating in the antenna dielectric material in the outer conductor recess, said antenna inner and outer conductors cooperating to emit the electromagnetic field sufficiently in a direction generally away from the flared interior wall of the antenna outer conductor.

17. The microwave ablation instrument of claim 16, wherein said line dielectric material includes a first dielectric constant, and the antenna dielectric material includes a second dielectric constant, and the distal face of the line dielectric material is spaced-apart from said proximal face thereof by a predetermined distance enabling resonance of the emitted electromagnetic field proportionately based upon the first dielectric constant and second dielectric constant.

18. The microwave ablation instrument of claim 17, wherein said outer conductor is conical-shaped, and said interior wall flares outwardly from the longitudinal axis at an acute angle in the range of about 15° to about 75°.

* * * * *